US00PP09710P

United States Patent [19]

Kramer

[11] Patent Number: Plant 9,710

[45] Date of Patent: Nov. 26, 1996

[54] HEATHER 'ALEXANDRA'

[76] Inventor: Kurt Kramer, Edanmer Strase 26, 26188 Edewecht, Germany

[21] Appl. No.: 459,510

[22] Filed: Jun. 2, 1995

[51] Int. Cl.[6] ..... A01H 5/00

[52] U.S. Cl. ..... Plt./54.1

[58] Field of Search ..... Plt./54.1

[56] References Cited

PUBLICATIONS

Huxley, A., et al. (Eds.) "*Calluna*" The New R.H.S. Dictionary of Gardening I, 1992, Stocton Press, N.Y. p. 469.

Bud–Flowering Heathers, article by David McClintock, published in the Garden, Nov. 1994, p. 543 (Table of Contents attached).

*Primary Examiner*—James R. Feyrer

*Attorney, Agent, or Firm*—Chernoff, Vilhauer, McClung & Stenzel

[57] ABSTRACT

A new and distinct variety of *Calluna vulgaris* Heather has purple flowers which remain as unopened buds through their entire cycle from fall through early spring.

3 Drawing Sheets

BACKGROUND AND SUMMARY OF THE INVENTION

The present invention relates to a new and disinct variety of bud flowering *Calluna vulgaris.* This new variety was developed by Kurt Kramer at Edewecht, Germany from a cross between two unpatented *Calluna vulgaris* developed by Mr. Kramer; No. 88-49-1 (seed parent) and 88-42-2 (pollen parent). The numbers were assigned to these varieties by Mr. Kramer. Both parents are marketed in Germany and both are *Calluna vulgaris* or "bud flowering" heathers. Cross pollination between bud flowering heathers is difficult since the flowers never open, but Mr. Kramer was able to do so to create the subject variety and its sister varieties 'Melanie' and 'Romina'. The resulting seeds were planted in 1991. From these seedlings 108 plants were selected and planted in a field. The subject plant of this disclosure was subsequently selected from these 108 seedlings. The subject variety has been asexually reproduced at Edewecht, Germany, from cuttings and subsequent generations have been true to form in all respects.

The subject variety produces buds in the fall having a unique purple color. The buds do not open into flowers but remain in the bud stage through the winter, approximately six months, from October to March, in Edewecht, Germany. The subject variety has a dense upright globular shape with protruding flower shoots which are heavily budded. The overall height of the plant at maturity, is approximately 24 inches with 6–8 inch shoots.

The closest varieties known to the applicant that have been publicly disclosed in Europe are 'Romina', a violet-red bud flowering Heather also developed by Kurt Kramer. To the best of applicant's knowledge, Romina has not been brought into the United States.

DETAILED DESCRIPTION OF THE NEW VARIETY

Figure 1:
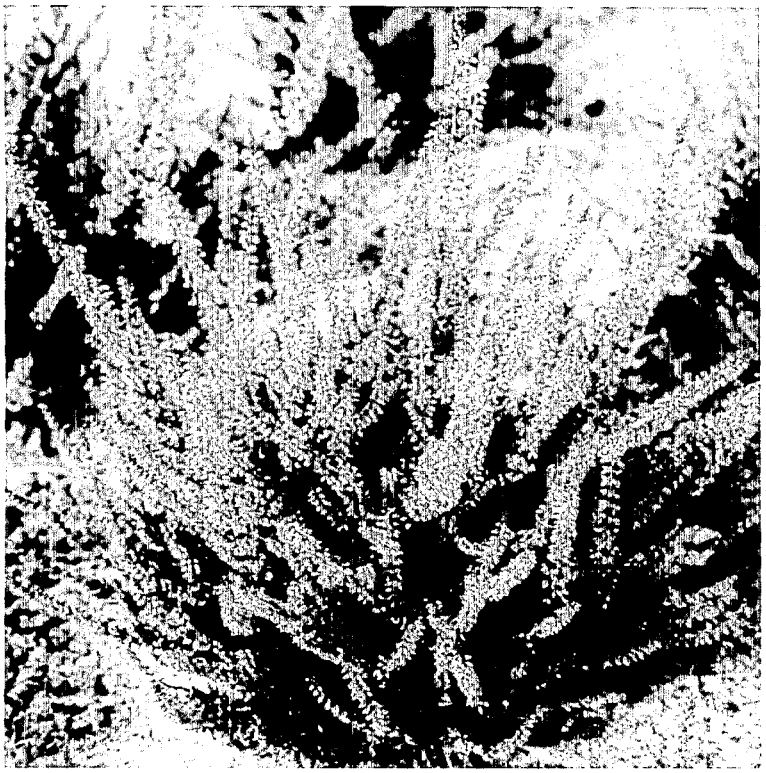
FIG. 1 shows the subject variety planted in the ground in Edewecht, Germany in October showing the color of the bud and shaped of the plant.
Figure 2:
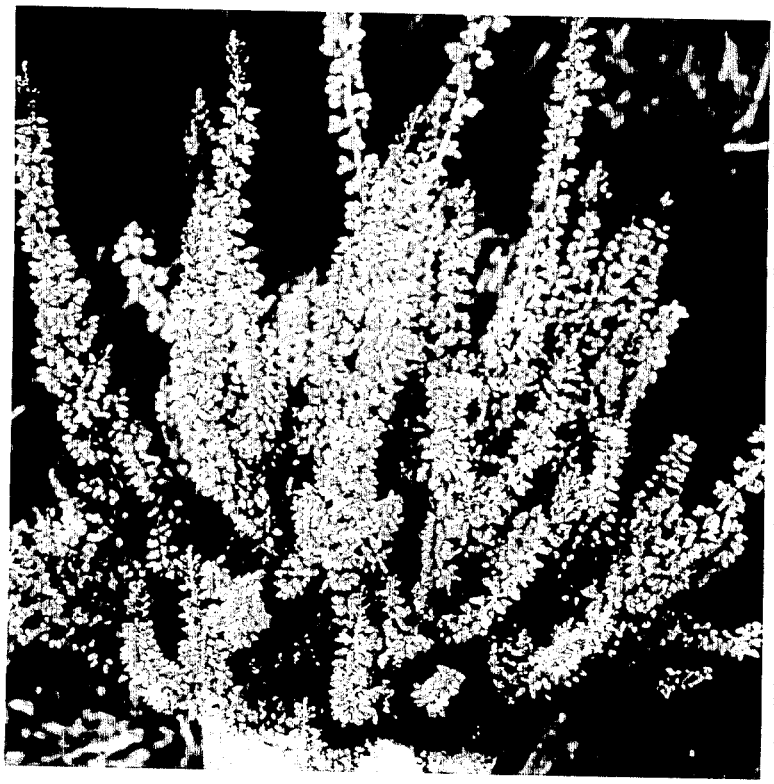
FIG. 2 shows the subject variety in a pot at about the same time period.
Figure 3:
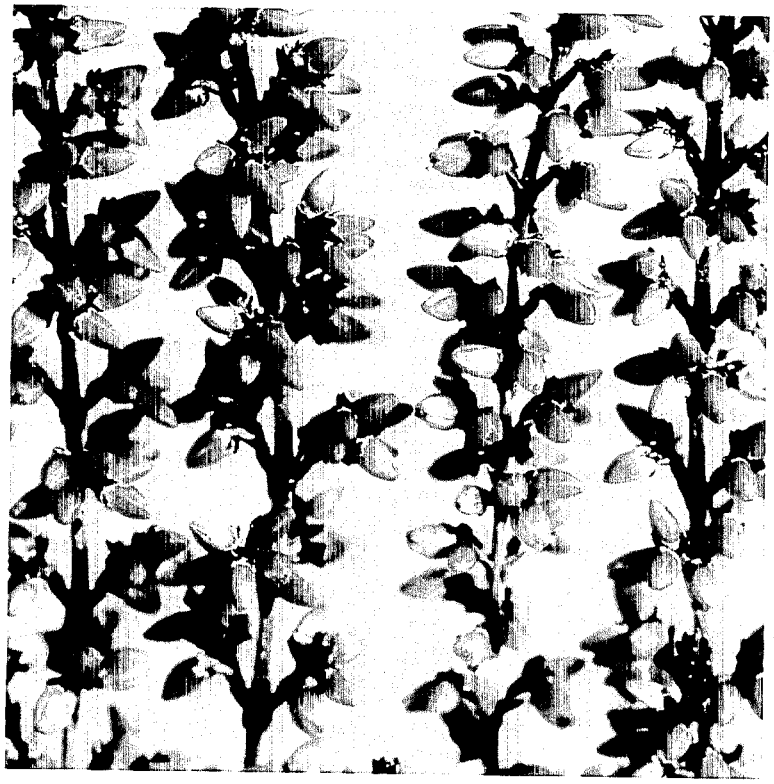
FIG. 3 shows the shoots and buds of the subject variety.

The following is a detailed description of the new variety of Heather plant based upon observations of plants grown at Edewecht, Germany. Color references are to *The Royal Horticultural Society Colour Chart* except where general color terms of ordinary dictionary significance are used.

PLANT

Botanical description: *Calluna vulgaris* (L.) Hull.

Common description: Broom Heather.

Form: Woody Shrub, perennial, evergreen.

Shape: Low, strongly basally branching shrub with very dense branching. Habit is generally mounded, with a profusion of weakly terminally dominant branches below flower spikes which occur at the apices of main branches.

Height: Approximately 24 inches, including flower spikes, at maturity.

Main stem:

*Length.*—Approximately 24 inches, including flower spikes, at maturity.

Color: Dark green 201A in April, tends to get lighter through the growing season.

Branching: Heavily branched until the spike. The spike has a plurality of auxiliary verticils of clusters of 2 to 4 buds outwardly radiating from the apices of oppositely placed, short branches arising out of leaf axils of bilobularly attached leaves, with stem pairs on a plane 90° to the plane of adjacent pairs.

Growth: Approximately 8 inches per year, very vigorous; ultimate height without spike is approximately 16 inches.

Foliage: Leaves are oppositely placed, scale-like and bractiolate, sessile, and occur in four rows on stems which are essentially square in cross-section.

*Leaf length.*—1–2 mm.

*Leaf width.*—0.3–1 mm.

*Leaf color.*—Color of plant ends in spring — light green 180A. Color of plant ends in winter — gray green 200B. Color of main plant in summer — blue green 188A.

Flower spikes: Formed at the terminals of main branches, having a plurality of uniformly spaced auxiliary verticils with clusters of 2 to 4, or more, mature buds outwardly radiating from the apex of oppositely placed, short branches which arise out of leaf axils of bilobularly attached bractiolate leaves; stem pairs are on a plane 90° to the plane of adjacent pairs. Length of spikes is normally about 6–8 inches, presenting a profusion of mature buds from base to the progressively bud-forming terminal. The number of buds formed is about average for the species.

Pruning: No Pruning is required except to maintain shape. Removal of spikes from the previous season will provide better growth of new spikes.

BUD

Color of bud at full development: Purple 61B-60B. The bud does not open to a flower. It stays a bud during its season.

Budding period: 6 months — fall through early spring.

Bud diameter: Approximately ⅛ inch.

Bud length: Approximately ¼ inch.

Bud shape: Truncated Elliptic.

Inflorescence: The corolla and reproductive organs of this plant are identical to those of the species. Corolla color — medium to light brown 165C. There are 4 sepals which fade after the first fruit. The plant does not produce seed because the style is covered by the sepals. Reproduction is by cutting.

What is claimed is:

1. A new and distinct variety of Heather plant named *Calluna vulgaris* 'Alexandra', substantially as herein shown and described, characterized particularly by its purple flowers which remain as an unopened bud from fall through early spring.

* * * * *